(12) United States Patent
Nuwayser

(10) Patent No.: US 7,041,320 B1
(45) Date of Patent: May 9, 2006

(54) HIGH DRUG LOADED INJECTABLE MICROPARTICLE COMPOSITIONS AND METHODS OF TREATING OPIOID DRUG DEPENDENCE

(75) Inventor: Elie S. Nuwayser, Woburn, MA (US)

(73) Assignee: Biotek, Inc., Woburn, MA (US)

( * ) Notice: Subject to any disclaimer, the term of this patent is extended or adjusted under 35 U.S.C. 154(b) by 116 days.

(21) Appl. No.: 10/159,559

(22) Filed: May 31, 2002

(51) Int. Cl.
*A61K 9/16* (2006.01)

(52) U.S. Cl. ............ 424/497; 424/489; 424/490; 424/501; 264/4.1; 264/4.3; 264/4.6

(58) Field of Classification Search ........ 424/489–501; 264/4.1, 4.3, 4.6
See application file for complete search history.

(56) References Cited

U.S. PATENT DOCUMENTS

| | | | |
|---|---|---|---|
| 3,523,906 A | 8/1970 | Hova et al. | 252/316 |
| 3,691,090 A | 9/1972 | Kitajima et al. | 252/316 |
| 3,737,337 A | 6/1973 | Wuppertal-Elberfeld et al. | 117/100 |
| 3,891,570 A | 6/1975 | Fukushima et al. | 252/316 |
| 3,960,757 A | 6/1976 | Morishita et al. | 252/316 |
| 4,389,330 A | 6/1983 | Tice et al. | 427/213.36 |
| 4,499,096 A | 2/1985 | Lotsof | 514/214 |
| 4,530,840 A | 7/1985 | Tice et al. | 514/179 |
| 4,542,025 A | 9/1985 | Tice et al. | 424/78 |
| 4,568,559 A | 2/1986 | Nuwayser et al. | 427/3 |
| 4,582,835 A | 4/1986 | Lewis et al. | 514/282 |
| 4,588,580 A | 5/1986 | Gale et al. | 424/21 |
| 4,623,588 A | 11/1986 | Nuwayser et al. | 428/402.24 |
| 4,675,189 A | 6/1987 | Kent et al. | 424/490 |
| 4,895,848 A | 1/1990 | Traber et al. | 514/255 |
| 4,897,268 A | 1/1990 | Tice et al. | 424/422 |
| 4,919,916 A | 4/1990 | Golwyn | 424/10 |
| 4,931,277 A | 6/1990 | Fontaine et al. | 424/195.1 |
| 4,935,428 A | 6/1990 | Lewis | 514/282 |
| 4,935,429 A | 6/1990 | Dackis et al. | 514/288 |
| 4,942,182 A | 7/1990 | Weiss et al. | 514/812 |
| 5,023,081 A * | 6/1991 | Trau et al. | 424/405 |
| 5,075,341 A | 12/1991 | Mendelson et al. | 514/282 |
| 5,100,916 A | 3/1992 | Johansson et al. | 514/478 |
| 5,124,340 A | 6/1992 | Jaffe et al. | 514/356 |
| 5,140,032 A | 8/1992 | Radecki | 514/221 |
| 5,149,538 A | 9/1992 | Granger et al. | 424/449 |
| 5,223,497 A | 6/1993 | Gawin et al. | 514/225.2 |
| 5,240,711 A | 8/1993 | Hille et al. | 424/448 |
| 5,256,669 A | 10/1993 | Askanazi et al. | 514/282 |
| 5,272,149 A | 12/1993 | Stalling | 514/255 |
| 5,298,622 A | 3/1994 | Portoghese et al. | 546/15 |
| 5,407,609 A | 4/1995 | Tice et al. | 264/46 |
| 5,500,227 A * | 3/1996 | Oshlack et al. | 424/476 |
| 5,648,097 A | 7/1997 | Nuwayser | 424/489 |
| 5,993,855 A * | 11/1999 | Yoshimoto et al. | 424/489 |
| 6,306,425 B1 | 10/2001 | Tice et al. | 424/426 |
| 6,495,155 B1 * | 12/2002 | Tice et al. | 424/426 |

OTHER PUBLICATIONS

Nuwayser et al., "Microencapsulation of Contraceptive Steroids," Proc. 11th Inter. Symp. Control. Rel. Bioactive Mater., pp. 71-72 (1984).*

(Continued)

*Primary Examiner*—Gollamudi S. Kishore
(74) *Attorney, Agent, or Firm*—Banner & Witcoff, Ltd.

(57) ABSTRACT

Methods and compositions to induce opioid drug independence in opioid drug dependent individuals comprising administering opioid agonists and/or antagonists encapsulated in biodegradable polymer microspheres in a dosage formulation.

20 Claims, 4 Drawing Sheets

Effect of Norvex™ Depot Buprenorphine SC Injection on VAS Drug Effect in Response to Opioid Challenge in 5 Heroin Addicts

OTHER PUBLICATIONS

Amory et al., "Testosterone Release from a Subcutaneous, Biodegradable Microcapsule Formulation (Viatrel) in Hypogonadal Men," *J. Andrology*, 23(1):84-91 (2002).

Comer et al., "Depot naltrexone: long-lasting antagonism of the effects of heroin in humans," *Psychopharmacology*, 159:351-360 (2002).

Kranzler et al., "Sustained-Release naltrexone for Alcoholism Treatment: A Preliminary Study," *Alcoholism: Clin. and Exp. Res.*, 22(5):1074-1079 (1998).

Leary, "Drug for Heroin Addiction Is Being marketed for Treatment of Alcoholism," *New York Times*, p. A18, Jan. 18, 1995.

Nath et al., "Buprenorphine Pharmacokinetics: Relative Bioavailability of Sublingual Tablet and Liquid Formulations," *J. Clin. Pharm.*, 39:619-623 (1999).

Nuwayser et al., "Microencapsulation of Contraceptive Steroids," *Proc. 11th Inter. Symp. Control. Rel. Bioactive Mater.*, pp. 71-72 (1984).

Nuwayser and DeRoo, "Microencapsulation with Microfluidized Beds," *Proc. 14th Inter. Symp. Control. Rel. Bioactive Mater.*, 2 pages (1987).

Nuwayser et al., "Sustained Release Injectable Naltrexone Microcapsules," *Proc. Inter. Symp. Control. Rel. Bioactive Mater.*, 15:201-202 (1988).

Nuwayser et al., "Sustained Release Injectable Methadone Microcapsules," *Proc. Inter. Symp. Control. Rel. Bioactive Mater.*, 16:83-84 (1989).

Nuwayser et al., "Sustained Release Injectable Naltrexone Microcapsules," *Proc. 52nd Ann. Sci. Meeting*, L. Harris, ed. NIDA Research Monograph 105, 532 (1991).

Nuwayser and Blaskovich, "In Vivo Studies of a One Month Injection for Buprenorphine," *Proc. Inter. Symp. Control. Rel. Bioactive Mater.*, 19:168-169 (1992).

Petry et al., "A comparison of four buprenorphine dosing regimens using open-dosing procedures: is twice-weekly dosing possible?" *Addiction*, 95(7):1069-1077 (2000).

Petry et al., "Examining the limits of the buprenorphine interdosing interval: daily, every-third-day and every-fifth-day dosing regimens," *Addiction*, 96(6):823-834 (2001).

Pfzyborowski et al., "Preparation of HSA Microspheres in a One-Step Thermal Denaturation of Protein Aerosol Carried in Gas-Medium," *Eur. J. Nuc. Med.*, 7:71-72 (1982).

Shah et al., "A biodegradable injectable implant for delivering micro and macromolecules using poly(lactic-co-glycolic)acid (PLGA) copolymers," *J. Controlled Release*, 27:139-147 (1993).

Williams et al., "Microencapsulated Local Anesthetics," *Proc. 11th Inter. Symp. Control. Rel. Bioactive Mater.*, pp. 69-70 (1984).

\* cited by examiner

Figure 1 : Buprenorphine Plasma Level in Monkeys
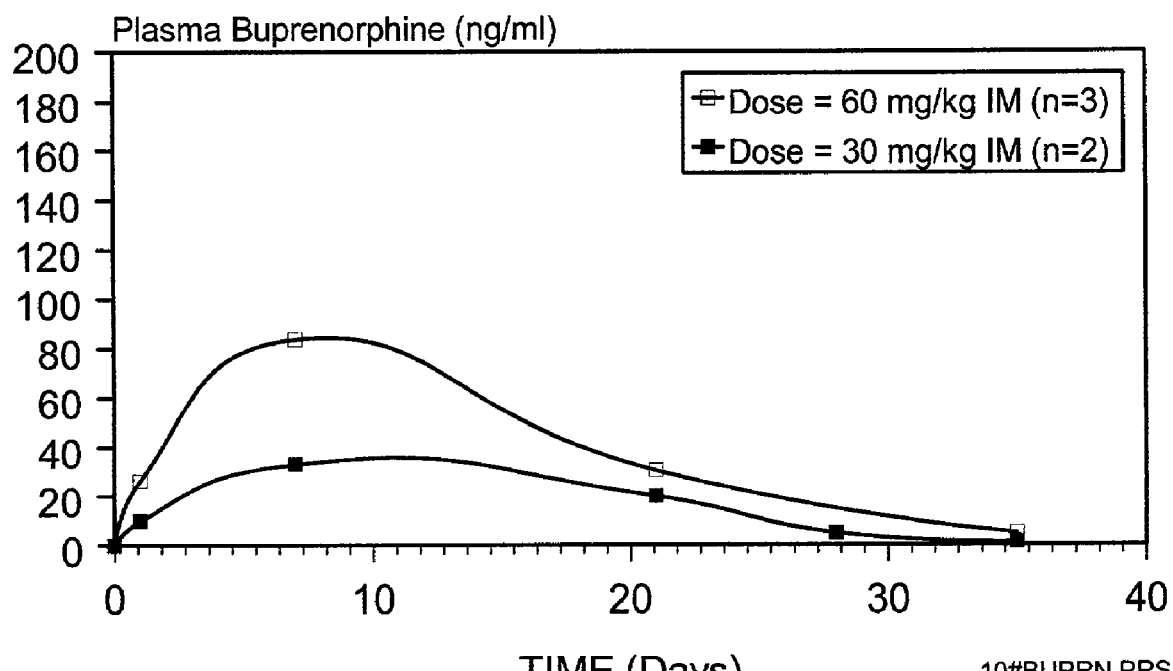

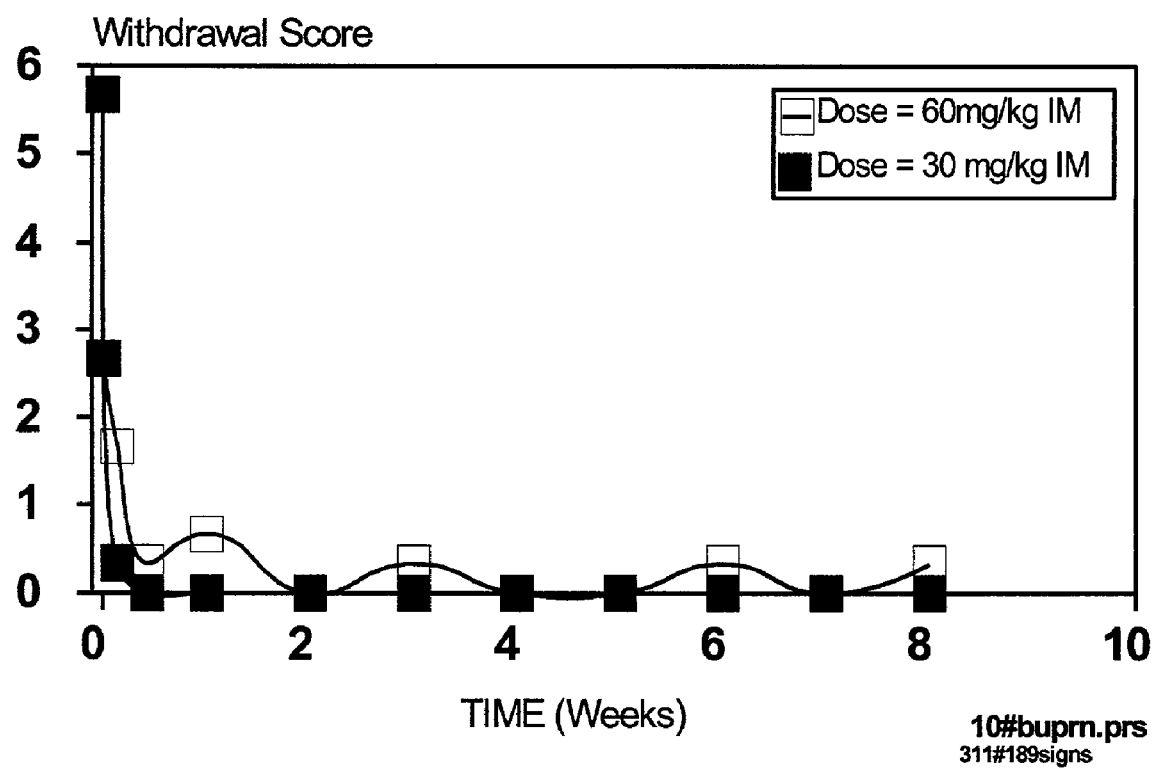
Figure 2: Effect of Buprenorphine Microcapsule Injection on Abruptly Withdrawn Morphine-Dependent Rhesus Monkeys

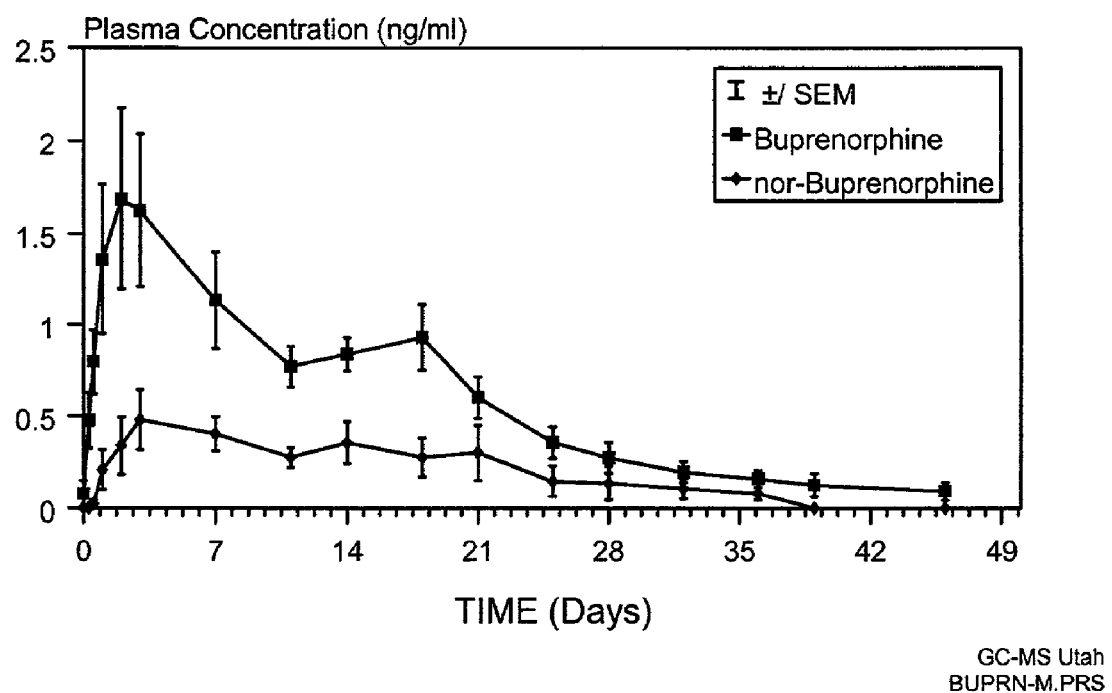
Figure 3: Plasma Level of Buprenorphine and nor-Buprenorphine in 5 Heroin Addicts Following SC Injection of Norvex™ Microcapsules Containing 58 mg Buprenorphine Base
GC-MS Utah
BUPRN-M.PRS

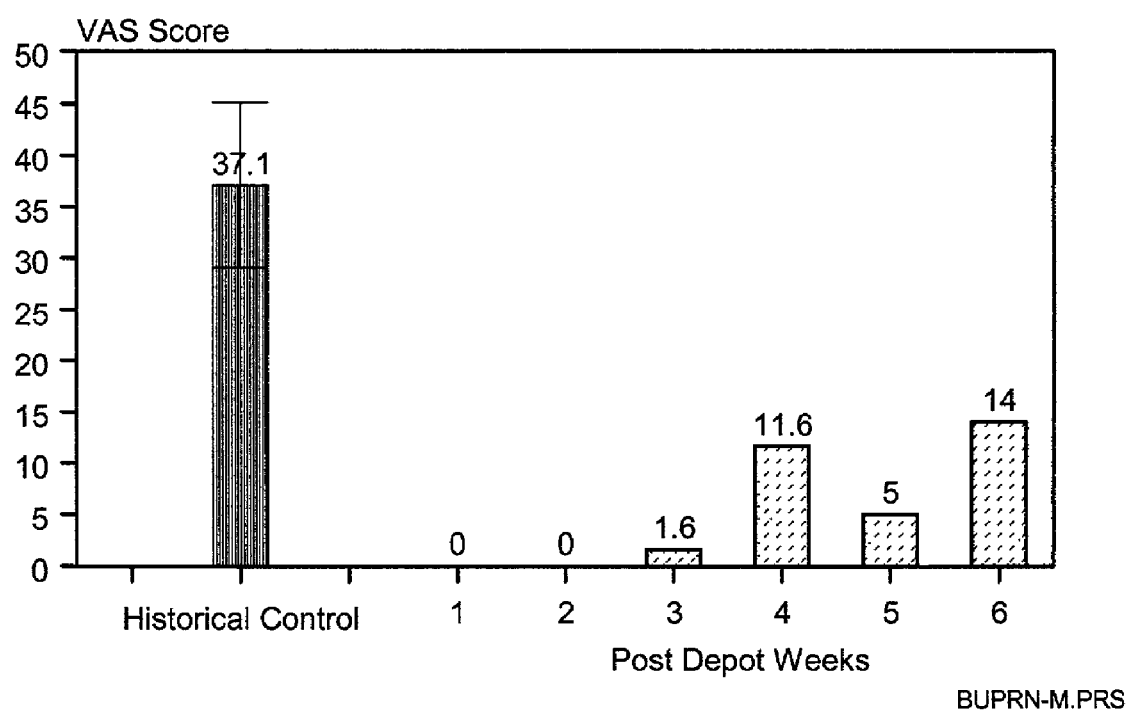
Figure 4 : Effect of Norvex™ Depot Buprenorphine SC Injection on VAS Drug Effect in Response to Opioid Challenge in 5 Heroin Addicts

HIGH DRUG LOADED INJECTABLE MICROPARTICLE COMPOSITIONS AND METHODS OF TREATING OPIOID DRUG DEPENDENCE

BACKGROUND OF THE INVENTION

1. Field of the Invention

Embodiments of the present invention relate generally to the field of treating addictions such as opioid drug additions. In particular, the present invention relates to a novel high drug loaded injectable microparticle, such as a microsphere or microcapsule (if a coating is included), including one or more active ingredients, such as an opioid agonist and/or partial opioid agonist compound. The novel microparticles are administered in a manner to promote the gradual release of an active ingredient, such as a drug, over an effective time period so as to serve as a treatment regimen for opioid dependent individuals.

2. Description of Related Art

Addiction to opioid drugs (opioids) by an individual is characterized by a dependence syndrome having both a strong psychological dependent aspect and a strong physical dependent aspect. The psychological dependent aspect typically is manifested by an overpowering compulsion on the part of the addict to continue taking opioids. This compulsion may be motivated in part by the development of a tolerance to opioids generally so that although one opioid may be substituted for another, the dosage of any opioid taken must be continually increased in order to obtain the initial psychological effect such as euphoria. Typically, an acute intoxication with opioids is characterized by euphoria, flushing, itching of the skin, miosis, drowsiness, decreased respiratory rate and depth, hypotension, bradycardia, and decreased body temperature.

Withdrawal of the drug or administration of an antagonist provokes a well known abstinence or withdrawal syndrome. Such a withdrawal syndrome generally includes symptoms and signs opposite to the drug's pharmacologic effects, e.g., central nervous system (CNS) hyperactivity. The severity of the withdrawal syndrome increases both with the size of the opioid dose used by the addict and the length of time the addict has used the opioid drug. Accordingly, a physical and/or psychological dependence on opioids develops to prevent experiencing the discomfort of the abstinence or withdrawal syndrome. In the case of heroin addiction, symptoms of withdrawal syndrome typically begin to appear as early as 4 to 6 hours after withdrawal (abstinence) from drug intake and reach a peak of severity within 36 to 72 hours. An initial anxiety and craving for the drug are followed by other symptoms of increasing severity and intensity. A characteristic early sign of withdrawal syndrome in addicted humans is an increased resting respiratory rate, >16/min, usually accompanied by yawning, perspiration, lacrimation, rhinorrhea, mydriasis, piloerection, tremors, muscle twitches, hot and cold flashes, aching muscles, and anorexia.

Tolerance and physical dependence on opioids can develop rapidly. For example, therapeutic doses of opioids, e.g., morphine, taken regularly over a 2- to 3-day period can lead to tolerance and physical dependence so that the user may show symptoms of withdrawal when the drug is discontinued.

Opioid drug use also induces cross-tolerance toward other opioid drugs, although such cross-tolerance may vary in degree from one opioid to another. Nevertheless, this property is the reason that addicts may substitute one opioid for another.

Various methods of treating addiction to opioid type drugs in individuals have been devised. A number of methods and compounds have been purported to be useful in treating the addict. For example, agonists are compounds that mimic the opioid and purportedly are useful in treating psychological dependence (tolerance) or physical dependence. Opioid agonists include methadone, buprenorphine and dopamine agonists, such as bromocriptine mesylate (see, U.S. Pat. No. 4,935,429). In the well known methadone substitution maintenance programs for heroin addiction, the heroin agonist methadone is administered orally at a dose that prevents substantial withdrawal syndrome and craving for opioid drugs. An attempt is then made to decrease the addict's dependence on the orally administered methadone. However, such weaning from orally administered methadone may, itself, be extremely difficult. Furthermore, addicts in such programs may abuse the use of the methadone, for example, by combining it with other drugs, and thereby simply transfer their heroin addiction to a methadone-based addiction.

A few compounds have been reported to act as antagonists of opioid addiction, for example, naloxone and naltrexone (see, e.g., O'Brien, C. P., et al., In *Problems of Drug Dependence,* 1982, NIDA Research Monograph 43, pages 71–78 (Harris, L. S., ed.) (DHHS Pub. (ADM) 82–1264, 1983); Rawson, R. A., et al., In *Problems of Drug Dependence* 1983, NIDA Research Monograph 49, pages 289–295 (Harris, L. S., ed.) (DHHS Pub. (ADM) 84–1316, 1984); Nuwayser, E. S., et al., *Proc. Intern. Symp. Control. Rel. Bioact. Mater.,* 15: 201–202 (1988)); buprenorphine (at certain concentrations) and spiroindane opiate analogs (U.S. Pat. No. 5,298,622). The primary uses of opioid antagonists have been in research and in therapies to reverse the toxic effects of opioids in cases of overdose. Such antagonists purportedly can bind to opioid receptors in the brain and thereby block the euphoric effect of opioids. Naltrexone is the only opioid antagonist currently approved by the Federal Drug Administration for use in the United States as a treatment of post addicts. Typically, the antagonist naltrexone is administered orally three times per week. Thus, as with methadone maintenance programs, regimens utilizing antagonists require the addict voluntarily to adhere to a rigidly controlled schedule of multiple administrations. Requiring the opioid addict strictly to adhere to a schedule of multiple administrations of a therapeutic compound over an indefinite period of time may be too onerous for most addicts to endure and may account for the fact that the current methods of treating opioid addiction have not proven to be widely successful at promoting a psychological and physical independence.

Microsphere compositions including naltrexone disclosed for use in reducing consumption of heroin and alcohol are known. See U.S. Pat. No. 6,306,425 hereby incorporated by reference in its entirety for all purposes. However, such microsphere compositions include less than 50% by weight of naltrexone, and therefore require large volumes of injectable formulations when treating drug addicted individuals. The formulations contemplate multiple administrations of the microspheres.

Accordingly, a need exists to provide a high drug loaded delivery vehicle for use in drug treatment programs. Such a high drug loaded delivery vehicle can provide a sustained release of an active ingredient over a prolonged period of time sufficient to reduce the withdrawal symptoms of opioid drug addicts and promote psychological and physical independence from the opioid drug.

SUMMARY OF THE INVENTION

Embodiments of the present invention are directed to microparticles that include greater than 50% by weight of the microparticle of one or more active ingredients effective in treating opioid addicts. For purposes of the present invention, the term "microparticle" includes microspheres and microcapsules. The term "microsphere" refers to a particle matrix including an active ingredient. The term "microcapsule" refers to a microparticle that includes one or more coatings on part or all of the microparticle. The active ingredient may be included in either the microparticle or coating or both. The active ingredient itself may be a coating. The coating serves to provide a desired release profile of the active ingredient into surrounding media.

In one embodiment, the invention provides microparticle including a biodegradable polymer matrix and buprenorphine in an amount greater than 50% by weight of the microparticle in an injectable dose formulation capable of providing sustained release of the buprenorphine in a manner to reduce opioid consumption in a human in need of opioid drug dependence treatment. In alternate embodiments, the active ingredient includes methadone or naltrexone. The microparticles of the present invention are used as drug delivery vehicles in an injectable formulation. Dosage formulations of the microparticles are prepared according to the present invention to allow for administration of the active ingredient over a prolonged period of time. According to one embodiment, the microparticles are formed from biodegradable polymers such as poly-L-lactide polymer (PLA), poly-L(-)lactide co-glycolide polymer (PLA-PGA), poly-L(-) lactide co-caprolactone polymer (PLA-PCL), or combinations thereof. The microparticles are injectable and biodegradable and permit a gradual and sustained release of the active ingredient into the patient's body for a period of time sufficient to treat the opioid drug dependence condition. Treatment objectives include lessening of withdrawal symptoms, reduction of drug consumption and/or eventual independence from drug craving and withdrawal syndrome.

BRIEF DESCRIPTION OF THE DRAWINGS

FIG. 1 is a graph of the serum buprenorphine levels in monkeys given a single depot dose of microcapsules including either 30 or 60 mg buprenorphine base/kg body weight.

FIG. 2 is a graph of the withdrawal score (indicating the degree of withdrawal syndrome by morphine-dependent monkeys) versus observation session (observation). Two withdrawal scores ("Pre Buprenorphine" and "Post Buprenorphine (2 Hr)") are given for the day on which buprenorphine-containing microcapsules were administered indicating the extent of withdrawal symptoms before and then 2 hours after administration of buprenorphine-containing microcapsules (30 or 60 mg buprenorphine base/kg body weight). Scoring continued at weekly intervals for 8 weeks.

FIG. 3 is a graph of the serum buprenorphine levels in heroin addicts given a single depot dose of microcapsules containing 58 mg buprenorphine base.

FIG. 4 is a graph of the effect of a single injection of microcapsules containing 58 mg of buprenorphine on visual analog scaling (VAS) drug effect in response to opioid challenge in five heroin addicts.

DETAILED DESCRIPTION OF CERTAIN PREFERRED EMBODIMENTS

According to the present invention, a microparticle including greater than 50% active ingredient by weight of the microparticle is provided in an injectable dosage formulation that is used in treating drug addiction. The microparticles can include both microspheres and microcapsules. The microcapsules are characterized by one or more coatings of a material to produce a desired release profile of the active ingredient into surrounding media. As a dosage formulation, the microparticles provide a gradual and sustained release of the active ingredient into patient plasma over a desired treatment period. Dosage formulations include less than 400 mg buprenorphine, 300 mg buprenorphine, 200 mg buprenorphine, 150 mg buprenorphine or less than 100 mg buprenorphine. Alternate dosage formulations include less than 75 mg buprenorphine and still alternate dosage formulations include less than 60 mg of buprenorphine, or less than 50 mg of buprenorphine, or less than 40 mg of buprenorphine, or less than 30 mg of buprenorphine, or less than 20 mg of buprenorphine, or less than 10 mg of buprenorphine.

Treatment periods within the scope of the present invention include periods greater than 3 days, greater than 7 days, greater than 30 days, greater than 42 days, greater than 90 days and greater than 120 days. Treatment periods generally are chosen between 7 and 42 days and depend in part on the severity of the opioid drug addition. The dosage formulations are prepared such that, in a preferred embodiment, a single injectable formulation provides a sustained release of the active ingredient within an individual over substantially the entire treatment period. While a single administration of the microparticles is preferred, additional administrations of the microparticles during a treatment period are also envisioned to prolong the sustained release of the active ingredient, to increase the amount of the active ingredient in the patient's plasma or to generally reduce withdrawal symptoms.

EXAMPLE I

Selection of a Pharmacologically Active Ingredient

The microparticles of the present invention contain a pharmacologically active ingredient including one or more opioid agonists, partial opioid agonists, one or more opioid antagonists, or combinations thereof. Opioid agonists mimic the effect of the opioid drug on which the addicted individual depends. Agonists which have been used in detoxification and maintenance therapies for drug addiction include methadone, buprenorphine and hydromorphone. Opioid antagonists include naltrexone, naloxone, and, at certain concentrations, buprenorphine, which bind mu, delta and/or kappa opioid receptors in the brain, thereby blocking the ability to experience the characteristic euphoria and other psychostimulant effects of opioids.

The major therapeutic uses of methadone are for analgesia and for treatment of opioid addicts (Jaffe et al., page 491, In *Pharmacological Basis of Therapeutics* (7th edition), (Gilman et al. eds.) (Macmillan, New York, 1985); Martin et al., pages 43–158, In *Handbook of Experimental Pharmacology, Drug Addiction I: Morphine, sedative/Hypnotic and Alcohol Dependence*, Vol. 451, (Martin, W. R., ed.) (Springer-Verlag, Berlin, 1977); Martin, et al., *Arch. Gen. Psychi.*, 28: 286–295 (1973)).

A number of studies have considered the optimum dose of methadone for the maintenance of post addicts (Horms et al., *Clin. Pharm. Exp. Ther.*, 17: 636 (1975); Verebely et al., *Res. Comm. Chem. Path. Pharm.*, 11: 373 (1975); Holmstrand et al., *Clin. Pharm. Exp. Ther.*, 23: 177 (1978)). The minimum oral dose of methadone is reported to be 30 mg/day, while results have been more consistent with a dose of at least 60 mg/day because of subject variability of the metabolism rate. The best record of rehabilitation was achieved when the plasma level was greater than 200 ng/ml (Holmstrand et al., *Clin. Pharm. Exp. Ther.*, 23: 177 (1978)).

Buprenorphine is a semi-synthetic opioid derived from thebaine. In receptor binding studies, it has been shown to bind to the mu and kappa opiate receptors like an antagonist with one fifth of the binding at delta receptors; agonist activity was found at the mu and kappa receptors (see, e.g., Kosten et al., *Life Sciences*, 42: 635 (1988)). Buprenorphine has relatively long lasting analgesic action at low doses with little clinically significant dependence liability or serious toxicity. Buprenorphine has been used to suppress heroin intake by heroin addicts (Mello et al., *Science*, 207(8): 657 (1980)) and has been shown to have opiate antagonist activity similar to naltrexone (Jasinski et al., *Arch. Gen. Psychiatry*, 35: 01(1978)). Buprenorphine has been reported to be effective in the detoxification of heroin addicts (Bickel et al., *Clin. Pharm. Thera.*, 43: 72 (1988)).

Because buprenorphine is both a partial opioid agonist and an opioid antagonist, it combines the advantages of both forms of pharmacotherapy. It is an analgesic with a duration of action similar to morphine but a 25 to 40-fold greater potency (Cowen et al., *Phamarc.*, 60: 537–545 (1977a); Cowen et al., *Pharmac.*, 60: 547–554 (1977b)). Its subjective effects resemble those of morphine and methadone in humans (Jasinski et al., *Arch. Gen. Psychiatry*, 35: 501 (1978)), and it is a positive reinforcer in primates (Mello et al., *J. Pharmacol. Exp. Ther.*, 216: 45–54 (1981)). As an opioid antagonist, a oral dose of 8 mg/day will antagonize morphine effects for more than 24 hours which is similar to the duration of naltrexone. Such a mixed agonist/antagonist opioid as buprenorphine is unique, since while blocking the effects of self-administered narcotics, a baseline euphoria is provided. In a human behavioral study, Mello and Mendelson (Mello et al., *Science*, 207(8): 657 (1980); Mello et al., *J. Pharma. Exp. Ther.*, 223(1): 30 (1982)) showed that buprenorphine decreased heroin self administration, did not cause opioid like withdrawal, and was preferred to methadone or naltrexone by the subjects.

In the case of maintenance treatment with buprenorphine, there are a number of studies of dose efficacy. The most commonly used dose form is a sublingual tablet. Nath et al. 1999 studied plasma levels of buprenorphine after 8 mg sublingual tablet doses. They found that the peak buprenorphine of 2.9 ng/ml was measured at 1.2 hours after dosing, then the level dropped to below 1.0 ng/ml after 6 hours and approached base line within 24 hrs. They found that the bioavailability from the sublingual tablet was around 30%.

Petry and co-workers evaluated various sublingual maintenance buprenorphine dosing regimens (doses given at one, three, four or five day intervals) in opioid-dependent human subjects and determined both opioid withdrawal symptoms and subject preference (Petry N M, Bickel W K, Badger G J., Addiction 2000 July; 95(7):1069–77) (Petry N M, Bickel W K, Badger G J., Addiction 2001 June; 96(6):823–34). The regimens were: 4 or 8 mg/70 kg every 24 hours, 8 or 16 mg/70 kg every 48 hours; 12 or 24 mg/70 kg every 72 hours; or 20 or 40 mg/70 kg every 120 hours. Opioid withdrawal ratings increased during the less frequent dosing schedules and withdrawal symptoms increased significantly during the every-fifth-day dosing regimen. Although there was increased discomfort, many more subjects preferred the quadruple-every-fourth-day dosing regimen over other options.

In reference to medical use of buprenorphine for control of pain, Hille U.S. Pat. No. 5,240,711 postulated that dependence on buprenorphine was likely to develop due to peaks of plasma buprenorphine, giving euphoria, followed by troughs of low plasma levels. Hille proposed a transdermal drug delivery system of one day delivery to extend the period between peaks and troughs.

EXAMPLE II

Selection of the Target Profile of Active Ingredient Delivery

According to the present invention, the microparticles include an active ingredient, such as buprenorphine, and a biodegradable polymer. The microparticles can be injected into an individual as a depot dose, using a convenient volume. The microparticles are designed to achieve a gradual release of the active ingredient over time. It is a characteristic of the invention that the rate of active ingredient delivered, and the duration of such delivery determine the outcome of treatment, such as achieving opioid independence. According to one aspect of the present invention, the active ingredient is delivered initially at a rate such that the addict does not experience extensive peaks of euphoria, yet sufficient agonist activity is present to prevent unpleasant opioid craving. According to an additional embodiment of the present invention, the active ingredient is delivered at a rate sufficient to reduce consumption of the opioid. According to an additional embodiment of the present invention, the rate of release of the active ingredient from the microparticles is substantially constant over the desired treatment period. According to an additional embodiment, the rate of release of the active ingredient from the microparticles into surrounding media decreases gradually over the desired treatment period. According to the above embodiments, the active ingredient is released into surrounding media in a controlled manner and preferably to avoid alternating peaks and valleys in the plasma concentration levels.

Typically, the calculation of the amount of active ingredient to be administered during a treatment period begins with knowledge of the recommended dose for a maintenance program involving the active ingredient. A time period over which theoretically one would like to maintain the gradual release of the pharmacologically active ingredient at the maintenance dose is selected and incorporated into the calculation for the amount of active ingredient to be included in the microparticles.

According to one aspect of the present invention, the microparticles, when administered by injection, provide a release profile for the active ingredient effective in treating opioid drug addicted individuals in a manner to reduce the consumption of the opioid drug. Importantly, the microparticles of the present invention when provided as an injectable dosage formulation provide improved bioavailability of the active ingredient when compared to oral or sublingual administration. Since the release of the active ingredient into plasma is achieved in a controlled and sustained manner over a substantial period of time by the injected microparticles, lesser amounts of active ingredient are administered to an individual during a desired treatment period when compared with oral or sublingual administration. For example, a person receiving 8 mg/day sublingual buprenorphine would take 240 mg of buprenorphine in 30 days. According to one aspect of the present invention, the microparticles can in a single dose include less than 75%, 50%, 25%, 10% and 5% of the total amount of opioid agonist and/or partial agonist doses currently recommended for opioid addiction maintenance or detoxification programs, that would be given over the desired period of release.

EXAMPLE III

Microparticle Preparation

Microparticles according to the present invention include one or more biodegradable polymer or copolymer materials and a pharmacologically active ingredient that constitutes greater than 50%, 60%, 70%, 75%, 80%, 85% or greater by weight of the microparticle. Alternatively, the active ingredient constitutes between 50% and 85%, preferably between 50% and 75% by weight of the microparticle. When the pharmacologically active agent is present in the microparticle at such percents by weight, the present invention allows one to prepare a dose formulation including sufficient active ingredient to treat drug addicted individuals over an extended period of time equal to known treatment periods to reduce opioid consumption.

The microparticles generally have a diameter within a range of between about 20 μm and about 200 μm, between about 50 μm and about 150 μm and preferably between about 40 μm and about 90 μm. The particles are preferably less than about 150 μm in diameter.

The microparticles of the present invention are made from one or more biodegradable polymer materials, such as those derived from the condensation of α-hydroxycarboxylic acids and related lactones which form aliphatic polyesters, including D or L optically active forms or DL optically inactive forms of poly-lactide (PLA), poly-lactide-co-glycolide (PLA-PGA) polymers, and poly-L-lactide-co-caprolactone (PLA-PCL) polymers. Other polymer materials that may be used in the methods and compositions of this invention include polymer materials which are formed from homo and co-polymers of mandelic acid, 3-propiolactone, tetramethylglycolide, butyrolactones, pivalolactone, intermolecular cyclid esters of α-hydroxy butyric acid, α-hydroxyisobutyric acid, α-hydroxyvaleric acid, α-hydroxyisovaleric acid, α-hydroxy caproic acid, α-hydroxy-α-ethylbutyric acid, α-hydroxyisocaproic acid, α-hydroxy-3-methylvaleric acid, α-hydroxyheptanoic acid, α-hydroxyoctanoic acid, α-hydroxydecanoic acid, α-hydroxymyristic acid, α-hydroxystearic acid, and α-hydroxylignoceric acid. Preferred polymer materials include poly-L-lactides (PLA) or poly-lactide:co-lactide (PLA-PGA) polymers. Once administered to an opioid drug addict in need of treatment to reduce consumption of the opioid drug, microparticles useful in the methods of the present invention permit a gradual and sustained release of their contents over time.

To produce the microcapsules of the present invention, one or more coatings are applied to a core particle or alternatively, an active ingredient is encapsulated by a coating which may then be further coated with additional coatings. Coating materials according to the present invention include the polymers described above as useful in making microspheres. The coatings of the present invention may include active ingredients or may be the active ingredients themselves. Coating materials also include other biodegradable polymers, lipids, gels, waxes and other coating materials well known to those of skill in the art of sufficient thickness and composition to control the rate of sustained release of active ingredient from the microcapsule. Coatings may include a water-leachable material such as a drug or even a plasticizer or pore forming material which is leached out during use to provide pores in the coating to increase the rate of release of active ingredient from the interior of the microcapsule. It is envisioned that one or more coatings may also be internal to the microcapsule and may separate active ingredient containing layers. Typically, where the polymer is a biodegradable polymer, the polymer would comprise a homo- or co-polymer of a glycolide or a lactide or monomer derivatives thereof. Methods of making microcapsules and in particular, materials and methods for providing coatings are described in companion patent application entitled "Multi-Layered Microcapsules and Method of Making Same," Ser. No. 10/161,130 filed concurrently herewith and incorporated by reference in its entirety for all purposes.

Methods of making microspheres containing pharmacologically active ingredients are known in the art. Typically, a polymer material is dispersed in a solvent and mixed with a solution containing the pharmacologically active compound, such as an opioid agonist and/or antagonist, to form a mixture or emulsion. When solvent is withdrawn from the mixture or emulsion, microspheres of the polymer material form encapsulating the pharmacologically active agent (see, e.g., U.S. Pat. No. 3,737,337). Other methods of making microspheres are provided in U.S. Pat. No. 3,523,906, U.S. Pat. No. 3,691,090, U.S. Pat. No. 3,891,570, U.S. Pat. No. 4,389,330, U.S. Pat. No. 4,530,840, U.S. Pat. Nos. 4,675,189 and 4,897,268 each of which are hereby incorporated by reference in its entirety.

Another method of preparing microspheres and microcapsules containing a pharmacologically active agent involves a microfluidized bed process (see, Nuwayser et al., Intern. Symp. Control. Rel. Bioact., 14: 304 (1987) and U.S. Pat. Nos. 4,568,559 and 4,623,588 hereby incorporated by reference in their entireties). A solution of the pharmacologically active ingredient and polymer is first prepared in an appropriate solvent and the solvent is evaporated leaving dry agent/polymer matrix, which is ground to form particles. The particles are then collected and used as a core material in an overcoating process. Microcapsules are formed by spraying the core particles with a solution of the polymer in a fluidized bed coating unit until a solid polymer wall of desired microspherical thickness is achieved.

For example, methadone-containing microcapsules were prepared by a two step process. In the first step, a cast core was prepared as follows: A solution of methadone base and polylactide polymer was prepared at a drug:polymer ratio of 3:1 in methylene chloride. The solution was placed in an evaporation dish and the solvent allowed to evaporate. The dry drug/polymer mixture was then ground, and the cast core particles between 50–150 μm were collected. In the second step, the cast core particles were overcoated with a solution of the polymer in methylene chloride to form microcapsules. The coating operation was conducted in a microfluidized bed microencapsulation unit as described in U.S. Pat. Nos. 4,568,559 and 4,623,588. Spraying of the polymer solution was continued until the total solids sprayed amounted to 18% of the weight of the cast core. The microcapsules were collected, washed in distilled water, and dried.

Microspheres containing buprenorphine were prepared using the above method where the polymer consisted of a 65:35 mixture of poly-lactide:co-glycolide polymer. A buprenorphine to polymer ratio of 4:1 was used to prepare the cast core particles. A final buprenorphine concentration of 76.9% was obtained. The cast core particles were then used to prepare microcapsules by spraying of polymer over the cast core particles until the total solids sprayed amounted to 3% of the weight of cast core.

Buprenorphine microspheres were prepared by solvent evaporation of a solution of buprenorphine base and a 65:35 mixture of poly-lactide:co-glycolide polymer as described above. The microspheres were collected through a set of stainless steel sieves and washed thoroughly with distilled water. Buprenorphine loading of 106–150 µm microspheres was 69.4%. The microspheres were converted by coating them with a polymer wall in a microfluidized bed microencapsulation unit as described in U.S. Pat. Nos. 4,568,559 and 4,623,588.

Once the microspheres have been prepared, the actual percent by weight which the pharmacologically active ingredient constitutes can be determined by routine analysis of a sample of the microspheres using high pressure liquid chromatography, as known in the art.

EXAMPLE IV

Administration of Microparticles Containing Active Ingredients

According to the present invention, high drug loaded microparticles are provided that can be prepared in injectable formulations for the controlled release of the active ingredient into surrounding media. The microparticles release the active ingredient over an extended period of time in a manner to produce plasma drug levels effective to reduce opioid consumption in an opioid addicted individual. The microparticles are biodegradable and biocompatible.

According to certain methods of the present invention, the microparticles are administered to an individual using a convenient fluid volume or suspending medium (e.g., between about 0.1 ml and about 10 ml, between about 2 ml and about 4 ml, between about 2 ml and about 3 ml, i.e. less than 5 ml per injection) and common syringe and needle size (e.g., 16–22-gauge needle). Typical injection volumes include 0.5 cc to 10 cc. The microparticles are preferably administered by injection, e.g., intravenously, subcutaneously, or intramuscularly. A pharmaceutically acceptable suspending medium is used to suspend the microparticles. The pharmaceutically acceptable suspending medium may be sterile water, phosphate buffered saline, a solution of carboxymethylcellulose or other convenient mediums for administering the microparticles. Other additives well known to those skilled in the art of formulating injectable formulations may also be included.

The microparticles used in the methods and compositions of the present invention permit a gradual release of their contents over time. Accordingly, a single dose can contain what is equivalent to multiple days worth of the daily amount of opioid agonist and/or antagonist currently recommended for opioid addiction maintenance or detoxification programs. For example, methadone-containing microparticles are preferably prepared to provide in a single dose of microparticles the equivalent of at least a seven days worth of the recommended daily amount of methadone used in maintenance programs. Buprenorphine-containing microparticles are preferably prepared to provide in a single dose the equivalent of at least 30 days worth of the recommended daily amount currently used in opioid addiction therapies.

Dosage formulations are prepared based on the drug content of the microparticles, the microparticle and the microparticle suspending medium. A dosage formulation can, if desired, be delivered by multiple injections. Microparticle density is calculated from the density of the drug and polymer, or it can be determined experimentally, and is usually greater than 1.0 g/cc. This is not unusual since the density of the drug and the polymer are both greater than 1.0 g/cc. The microparticles are formulated in an appropriate medium to provide from about 25 to 400 mg of active ingredient such as buprenorphine per injectable formulation, including 30 to 60 mg of active ingredient such as buprenorphine. Subsequent to administration, the individual may be monitored for active ingredient plasma concentration to ensure that a therapeutically effective plasma concentration is being maintained. Suitable plasma concentrations range from 0.05 ng/ml to 2.0 ng/ml. When the active ingredient plasma concentration falls below a therapeutic range, a subsequent injection may be made and the process repeated during the treatment period.

The maximum concentration of delivery vehicles in the suspending medium which can be delivered through a 20 gauge needle is usually 25% (w/v). Higher concentrations of delivery vehicles tend to plug the needle and increase the force required for injection. Higher concentrations can be used if the size of the needle is increased to 18 gauge.

To insure that a sufficient quantity of delivery vehicles is present in each vial, an excess amount of delivery vehicles is placed in a 10 ml glass vial approved for clinical use by the United States Food and Drug Administration (FDA). The vials are covered and sterilized by gamma radiation. A separate 10 ml vial will contain sterile suspending medium. The microspheres are reconstituted immediately before injection by adding the appropriate volume of suspending medium to give the final desired concentration of the drug.

EXAMPLE V

A Single Depot Dose of Microcapsule Containing Buprenorphine Induces Independence from Opioid Drug Addiction in Rhesus Monkey Primates Six male and female rhesus monkeys (*Macaca mulatta*), weighing at least 2 kg when received and certified to be in good health were purchased from a licensed supplier and kept in quarantine for 60–90 days. Each monkey was trained to leave its pen and receive 3.0 mg/kg morphine sulfate administered s.c. every 6 hour. The monkeys were maximally dependent, i.e., they had received morphine every 6 hours for at least 90 days before being used. When morphine was abruptly withdrawn, abstinence signs were scored.

Buprenorphine microcapsules including 76.9% buprenorphine by weight were administered to each monkey in a single depot parenteral dose. Three monkeys received doses of 30 mg buprenorphine base/kg body weight and three monkeys received doses of 60 mg buprenorphine/kg body weight. The doses were prepared by the addition of a sterile suspending medium consisting of carboxymethylcellulose in water to a vial containing a known weight of microcapsules. After mixing with a vortex mixer, the volume of suspension needed, based on body weight, was immediately drawn into a syringe equipped with an 18 gauge needle, and one-half of that volume was injected into the quadriceps muscles of each thigh.

Blood was drawn from each monkey before the buprenorphine microcapsule injection, again at 2 and 24 hours post-injection, and at weekly intervals thereafter. Plasma buprenorphine content was measured by GC-MS. FIG. 1 shows the plasma buprenorphine levels of the two groups of monkeys in the study as initially rising and then gradually decreasing over time. The figure shows that the plasma buprenorphine levels correlate with total dose given. Also, plasma buprenorphine was detected for approximately 30 days for the lower dose group and for 35–40 days for the higher dose group.

FIG. 2 shows the effect of administering a single depot dose of buprenorphine-containing microcapsules on abruptly withdrawn morphine-dependent rhesus monkeys. Because dose-related effects were not apparent, the data from all six monkeys were combined. Treatment with the buprenorphine microcapsule preparations attenuated abrupt withdrawal after 2 hours. The buprenorphine-containing microcapsule preparation quickly alleviated withdrawal in monkeys maximally dependent on morphine. While suppression was not complete at 2 hour, the monkeys did not appear to be in distress and behaved normally by 24 hours. The duration of alleviation of withdrawal continued beyond the period of detection of plasma buprenorphine, and the monkeys appeared after the single dose to be opioid independent.

At the end of the study, morphine sulfate (3.0 mg/kg) was given to determine whether loss of tolerance had occurred. The monkeys were scored for overt behavioral signs commonly noted in non-dependent monkeys receiving this dose for the first time. The signs were: ataxia, body sag, drowsiness, ptosis, scratching, and slowing. Loss of tolerance to morphine was demonstrated at the end of the study.

EXAMPLE VI

A Single Depot Dose of Microcapsules Containing Buprenorphine Induces Independence from Opioid Drug Addiction in Human Volunteers Clinical Procedures—Volunteers were five physically-dependent opioid abusers seeking or willing to accept opioid detoxification, and who provided their written informed consent to research participation. Mean duration of heroin use in these volunteers was 6.6 years. After one day of treatment for suppression of the opioid abstinence syndrome with oral hydromorphone (Dilaudid®), as judged clinically appropriate by an internist, each volunteer received a morning subcutaneous depot injection containing 58 mg of buprenorphine base. Volunteers remained in the residential unit through week 4; weeks 5 and 6 were as outpatients with urine toxicology samples being collected weekly and self-reports of drug use being collected twice weekly. Blood samples were collected periodically and each sample was analyzed for plasma buprenorphine and nor-buprenorphine concentrations.

Plasma Levels—The results are presented in FIG. 3, which show the level of buprenorphine and nor-buprenorphine metabolite. Following subcutaneous depot injection, the plasma level of buprenorphine increased rapidly and reached a maximum of 1.684 ng/ml after two days. After this, the level declined slowly to nearly zero 47 days after the injection. The average level over the 47 day period was 0.676 ng/ml (range 0.076–1.684). The nor-buprenorphine level reached a peak of 0.48 ng/ml after 3 days. The level remained between 0.27 and 0.48 ng/ml for 21 days, and then declined to zero 39 days after the injection. The average level over the 39 day period was 0.18 ng/ml (range 0–0.48 ng/ml).

The depot buprenorphine appeared safe and well-tolerated. There were no serious adverse events. There were no occasions of respiratory depression detected by pulse oximetry; oxygen saturation remained above 95%. There was no evidence of significant opioid intoxication suggestive of sedation or behavioral impairment. Most importantly, there was no evidence of a buprenorphine withdrawal syndrome as the plasma level declined.

Volunteers were assessed periodically over 6 weeks for signs and symptoms of opioid agonist effects and/or of opioid withdrawal by self-report ratings on an adjective rating scale sensitive to opioid withdrawal. At weeks 1, 2, 3, 4, 5, and 6 after depot administration volunteers participated in opioid challenge test sessions to assess response to placebo versus 3 mg hydromorphone given subcutaneously (double-blind, random order). This opioid challenge dose is equivalent to approximately 20–25 mg of parenteral morphine. Effects of the challenge doses were assessed with visual analog rating scales of subjective effects as shown in FIG. 4.

Subjective rating scale scores reflective of withdrawal symptoms were elevated for all 5 patients during the pre-depot period, declined on the depot day, and then remained steady at near-zero levels throughout the 4-week post-depot period. At post-dose weeks 1 and 2 the peak visual analog scale (VAS) rating of "Do you feel any drug effect?" was zero for all five volunteers (zero variability). Mean ratings gradually increased over weeks 3–6—from 1.6, to 11.6, to 5.0, to 14.0. Historically, opioid users challenged with this same hydromorphone dose have a mean peak response on this question of 37.1 (SEM=8.0). Thus, depot buprenorphine was very effective in dramatically reducing responsiveness to exogenous opioid challenge for a duration of at least several weeks.

Another index of the efficacy of depot buprenorphine in suppressing the opioid withdrawal syndrome is the amount of hydromorphone required to achieve withdrawal suppression after depot administration. For all subjects hydromorphone administration was judged to be clinically indicated prior to depot administration, but not after. The mean amount of oral hydromorphone administered after residential admission and prior to depot administration was 44 mg and the mean time interval over which it was administered (time from first to last dose) was 9 hours.

All five participants successfully achieved opioid detoxification, defined as completing the 4-week post-depot residential phase without additional opioid medications, without other medications for withdrawal relief, and without clinically significant withdrawal signs or symptoms. During the subsequent 2-week outpatient phase all patients reported abstinence from opioids and urine toxicology samples were negative for opioids.

While the foregoing discussion, embodiments, and examples are intended to be exemplary as to the scope and practice of this invention, it is apparent that numerous alterations may be made without departing from the spirit of this invention.

What is claimed is:

1. A method of making coated microparticles comprising
   mixing a biodegradable polymer, buprenorphine, methylene chloride and dimethyl sulfoxide to form an organic phase,
   mixing the organic phase with an aqueous phase to form an emulsion,
   maintaining the emulsion for a period of time sufficient to form hardened microparticles,
   recovering the microparticles, and
   coating the microparticles with a coating polymer to form a polymer coating in an amount between 0.1 to 85 percent by weight of the microparticles wherein the biodegradable polymer is a member selected from the group consisting of D or L optically active forms or DL optically inactive forms of poly-lactide (PLA), poly-lactide-co-glycolide (PLA-PGA) polymers and poly-L-lactide-co-caprolactone (PLA-PCL) polymers.

2. The method of claim 1 wherein the polymer coating is in an amount of 14% or less by weight of the microparticles.

3. The method of claim 1 wherein the polymer coating is in an amount of 10% or less by weight of the microparticles.

4. The method of claim 1 wherein the coating polymer is in an amount of 3% or less by weight of the microparticles.

5. The method of claim 1 wherein the buprenorphine is in an amount of greater than 50% by weight of the microparticles.

6. The method of claim 1 wherein the buprenorphine is in an amount of greater than 70% by weight of the microparticles.

7. The method of claim 1 wherein the buprenorphine is in an amount of greater than 75% by weight of the microparticles.

8. The method of claim 1 wherein the buprenorphine is in an amount of greater than 80% by weight of the microparticles.

9. The method of claim 1 wherein the buprenorphine is in an amount of greater than 85% by weight of the microparticles.

10. The method of claim 1 wherein the coating polymer is D or L optically active forms or DL optically inactive forms of poly-lactide (PLA), poly-lactide-co-glycolide (PLA-PGA) polymers, or poly-L-lactide-co-caprolactone (PLA-PCL) polymers.

11. Coated microparticles made according to a process comprising
mixing a biodegradable polymer, buprenorphine, methylene chloride and dimethyl sulfoxide to form an organic phase,
mixing the organic phase with an aqueous phase to form an emulsion,
maintaining the emulsion for a period of time sufficient to form hardened microparticles,
recovering the microparticles, and
coating the microparticles with a coating polymer to form a polymer coating in an amount between 0.1 to 85 percent by weight of the microparticles wherein the biodegradable polymer is a member selected from the group consisting of D or L optically active forms or DL optically inactive forms of poly-lactide (PLA), poly-lactide-co-glycolide (PLA-PGA) polymers and poly-L-lactide-co-caprolactone (PLA-PCL) polymers.

12. The coated microparticles of claim 11 wherein the polymer coating is in an amount of 14% or less by weight of the microparticles.

13. The coated microparticles of claim 11 wherein the polymer coating is in an amount of 10% or less by weight of the microparticles.

14. The coated microparticles of claim 11 wherein the coating polymer is in an amount of 3% or less by weight of the microparticles.

15. The coated microparticles of claim 11 wherein the buprenorphine is in an amount of greater than 50% by weight of the microparticles.

16. The coated microparticles of claim 11 wherein the buprenorphine is in an amount of greater than 70% by weight of the microparticles.

17. The coated microparticles of claim 11 wherein the buprenorphine is in an amount of greater than 75% by weight of the microparticles.

18. The coated microparticles of claim 11 wherein the buprenorphine is in an amount of greater than 80% by weight of the microparticles.

19. The coated microparticles of claim 11 wherein the buprenorphine is in an amount of greater than 85% by weight of the microparticles.

20. The coated microparticles of claim 11 wherein the coating polymer is D or L optically active forms or DL optically inactive forms of poly-lactide (PLA), poly-lactide-co-glycolide (PLA-PGA) polymers, or poly-L-lactide-co-caprolactone (PLA-PCL) polymers.

* * * * *